United States Patent
Hatano

(10) Patent No.: US 10,524,642 B2
(45) Date of Patent: Jan. 7, 2020

(54) BENDING OPERATION DEVICE AND ENDOSCOPE

(71) Applicant: OLYMPUS CORPORATION, Tokyo (JP)

(72) Inventor: Keisuke Hatano, Koganei (JP)

(73) Assignee: OLYMPUS CORPORATION, Tokyo (JP)

( * ) Notice: Subject to any disclaimer, the term of this patent is extended or adjusted under 35 U.S.C. 154(b) by 100 days.

(21) Appl. No.: 15/624,761

(22) Filed: Jun. 16, 2017

(65) Prior Publication Data

US 2017/0280973 A1 Oct. 5, 2017

Related U.S. Application Data

(63) Continuation of application No. PCT/JP2016/061030, filed on Apr. 4, 2016.

(30) Foreign Application Priority Data

Jun. 8, 2015 (JP) .................................. 2015-116100

(51) Int. Cl.
  *A61B 1/00* (2006.01)
  *A61B 1/005* (2006.01)
(52) U.S. Cl.
  CPC .......... *A61B 1/0057* (2013.01); *A61B 1/0052* (2013.01)
(58) Field of Classification Search
  CPC .................................................... A61B 1/0052
  (Continued)

(56) References Cited

U.S. PATENT DOCUMENTS

2003/0092965 A1  5/2003 Konomura et al.
2008/0207998 A1* 8/2008 Maruyama ........... A61B 1/0052
                                                600/114
(Continued)

FOREIGN PATENT DOCUMENTS

CN       103547208 A    1/2014
CN       107072481 A    8/2017
(Continued)

OTHER PUBLICATIONS

International Search Report dated Jun. 21, 2016 issued in PCT/JP2016/061030.
(Continued)

*Primary Examiner* — Alexandra L Newton
*Assistant Examiner* — Rynae Boler
(74) *Attorney, Agent, or Firm* — Scully, Scott, Murphy & Presser, P.C.

(57) ABSTRACT

A bending operation device includes a bending lever that is tiltably supported with an angle to a longitudinal direction of an operation section of an endoscope, a wire pulling member that includes a plurality of arm portions that are displaced according to tilting motion of the bending lever, a plurality of operation wires that are connected to the plurality of arm portions and that bend a bending portion provided in an insertion section of the endoscope according to displacement of the wire pulling member, and a plurality of pulleys that guide the plurality of operation wires to the plurality of arm portions, with the plurality of operation wires being substantially parallel to one another, when the bending lever is in a neutral position at which the bending portion is substantially straight.

5 Claims, 12 Drawing Sheets

(58) Field of Classification Search
USPC .......................................... 600/146; 74/89.22
See application file for complete search history.

(56) References Cited

U.S. PATENT DOCUMENTS

| | | | |
|---|---|---|---|
| 2012/0085956 A1* | 4/2012 | Morimoto | A61B 1/00068 |
| | | | 251/324 |
| 2013/0047755 A1 | 2/2013 | Okamoto | |
| 2013/0047757 A1* | 2/2013 | Okamoto | A61B 1/0016 |
| | | | 74/89.22 |
| 2013/0331652 A1 | 12/2013 | Okamoto | |
| 2014/0309625 A1 | 10/2014 | Okamoto et al. | |

FOREIGN PATENT DOCUMENTS

| | | |
|---|---|---|
| EP | 2649921 A1 | 10/2013 |
| EP | 3 192 426 A1 | 7/2017 |
| JP | 2007-325958 A | 12/2007 |
| JP | 2010-207598 A | 9/2010 |
| JP | 5877279 B2 | 3/2016 |
| WO | WO 2012/117836 A1 | 9/2012 |
| WO | WO 2015/068468 A1 | 5/2015 |

OTHER PUBLICATIONS

English Abstract of EP 3047786 A1, dated Jul. 27, 2016.
Extended Supplementary European Search Report dated Jun. 25, 2018 in European Patent Application No. 16 80 7192.6.

* cited by examiner

BENDING OPERATION DEVICE AND ENDOSCOPE

CROSS REFERENCE TO RELATED APPLICATION

This application is a continuation application of PCT/JP2016/061030 filed on Apr. 4, 2016 and claims benefit of Japanese Application No. 2015-116100 filed in Japan on Jun. 8, 2015, the entire contents of which are incorporated herein by this reference.

BACKGROUND OF INVENTION

1. Field of the Invention

The present invention relates to a bending operation device which causes a bending portion to be bent in accordance with a tilting operation of a bending lever, and an endoscope.

2. Description of the Related Art

Conventionally, endoscopes which can be inserted into a subject or an object are widely used in medical and industrial fields, for example, in order to observe a position inside the subject or the object where observation is difficult, such as the inside of a living body or the inside of construction.

A bending portion for increasing the insertability and observation performance inside the subject or the object is provided in an insertion section of such an endoscope. The bending portion is bent by a bending operation device provided in an operation section.

For example, Japanese Patent Application Laid-Open Publication No. 2007-325958 discloses a joystick-type tubular operation device as a bending operation device for bending a bending portion of an insertion section.

With respect to a conventional bending operation device, a technique is disclosed according to which, in order to reduce the amount of operation force for pulling an operation wire connected to a joystick-type operation lever, the bending operation device is provided with a motor that rotates a pulley around which a mid-portion of the operation wire is wound in a slackened state, and causes a bending portion to operate.

SUMMARY OF THE INVENTION

A bending operation device according to an aspect of the present invention includes: a bending lever that is tiltably supported with an angle to a longitudinal direction of an operation section of an endoscope; a wire pulling member that is provided inside the operation section, and includes a plurality of arm portions that are displaced according to tilting motion of the bending lever; a plurality of operation wires that are connected to the plurality of arm portions, and bend, by being pulled/slackened according to displacement of the wire pulling member, a bending portion that is provided in an insertion section of the endoscope; and a plurality of pulleys that are provided inside the operation section, and guide the plurality of operation wires to the plurality of arm portions, with the plurality of operation wires being substantially parallel to one another, when the bending lever is in a neutral position at which the bending portion is substantially straight, wherein at least two of the pulleys configured to change directions of two of the operation wires for bending the bending portion upward are disposed on a same rotation shaft.

A bending operation device according to another aspect of the present invention includes: a bending lever that is tiltably supported with an angle to a longitudinal direction of an operation section of an endoscope; a wire pulling member that is provided inside the operation section, and includes a plurality of arm portions that are displaced according to tilting motion of the bending lever; a plurality of operation wires that are connected to the plurality of arm portions, and bend, by being pulled/slackened according to displacement of the wire pulling member, a bending portion that is provided in an insertion section of the endoscope; and a plurality of pulleys that are provided inside the operation section, and guide the plurality of operation wires to the plurality of arm portions, with the plurality of operation wires being substantially parallel to one another, when the bending lever is in a neutral position at which the bending portion is substantially straight, wherein two of the pulleys configured to change directions of two of the operation wires for bending the bending portion upward are pivotally supported by a same rotation shaft, and two of the pulleys that are different from the two pulleys and that are configured to change directions of two of the operation wires that are different from the two operation wires and that are for bending the bending portion downward are pivotally supported by a same rotation shaft.

A bending operation device according to another aspect of the present invention includes: a bending lever that is tiltably supported with an angle to a longitudinal direction of an operation section of an endoscope; a wire pulling member that is provided inside the operation section, and includes a plurality of arm portions that are displaced according to tilting motion of the bending lever; a plurality of operation wires that are connected to the plurality of arm portions, and bend, by being pulled/slackened according to displacement of the wire pulling member, a bending portion that is provided in an insertion section of the endoscope; and a plurality of pulleys that are provided inside the operation section, and guide the plurality of operation wires to the plurality of arm portions, with the plurality of operation wires being substantially parallel to one another, when the bending lever is in a neutral position at which the bending portion is substantially straight, wherein a cylinder of a suction valve is provided in the operation section, and the wire pulling member is arranged at a position rotated around a center axis of the bending lever so that the plurality of arm portions and the cylinder do not interfere with each other.

In addition, an endoscope according to one aspect of the present invention includes one of the above-described bending operation devices.

DETAILED DESCRIPTION OF THE PREFERRED EMBODIMENT(S)

Figure 3:
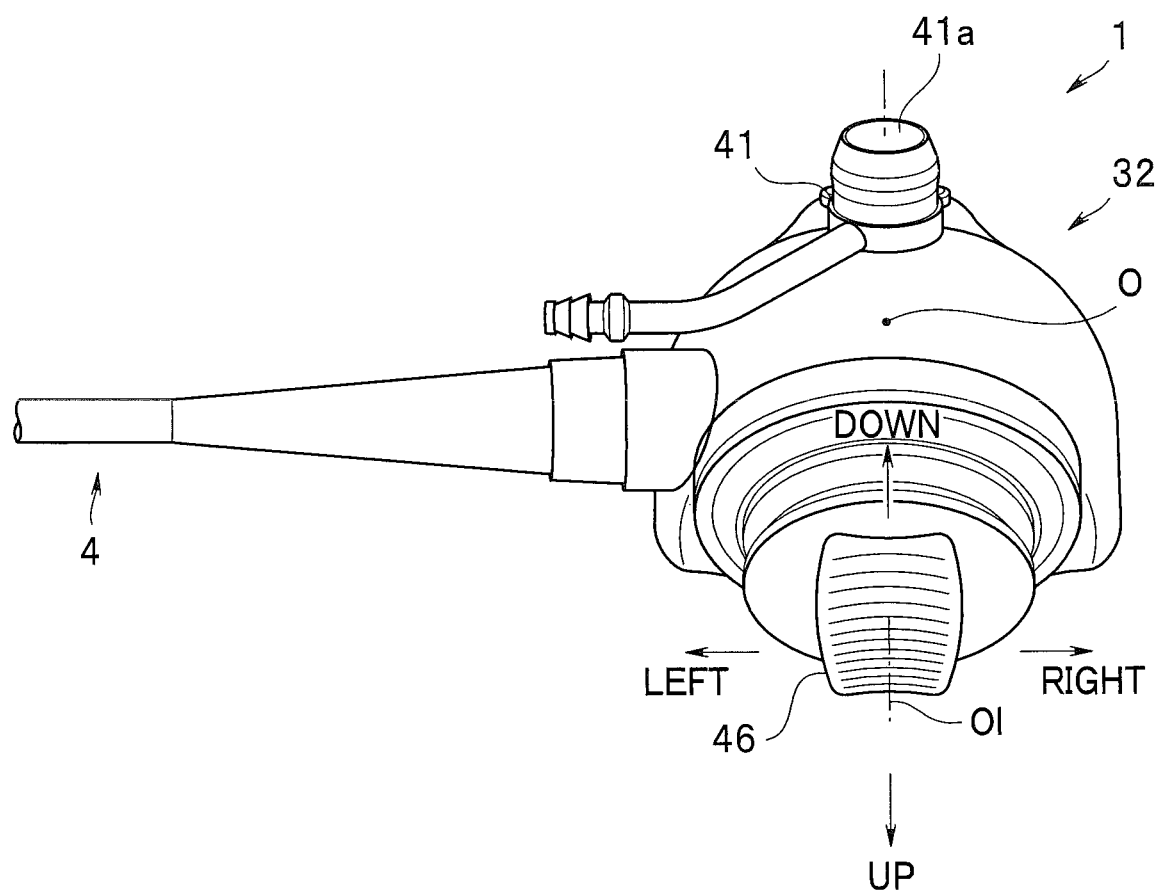
FIG. 3 is a top view showing the external appearance of the endoscope.
Figure 4:
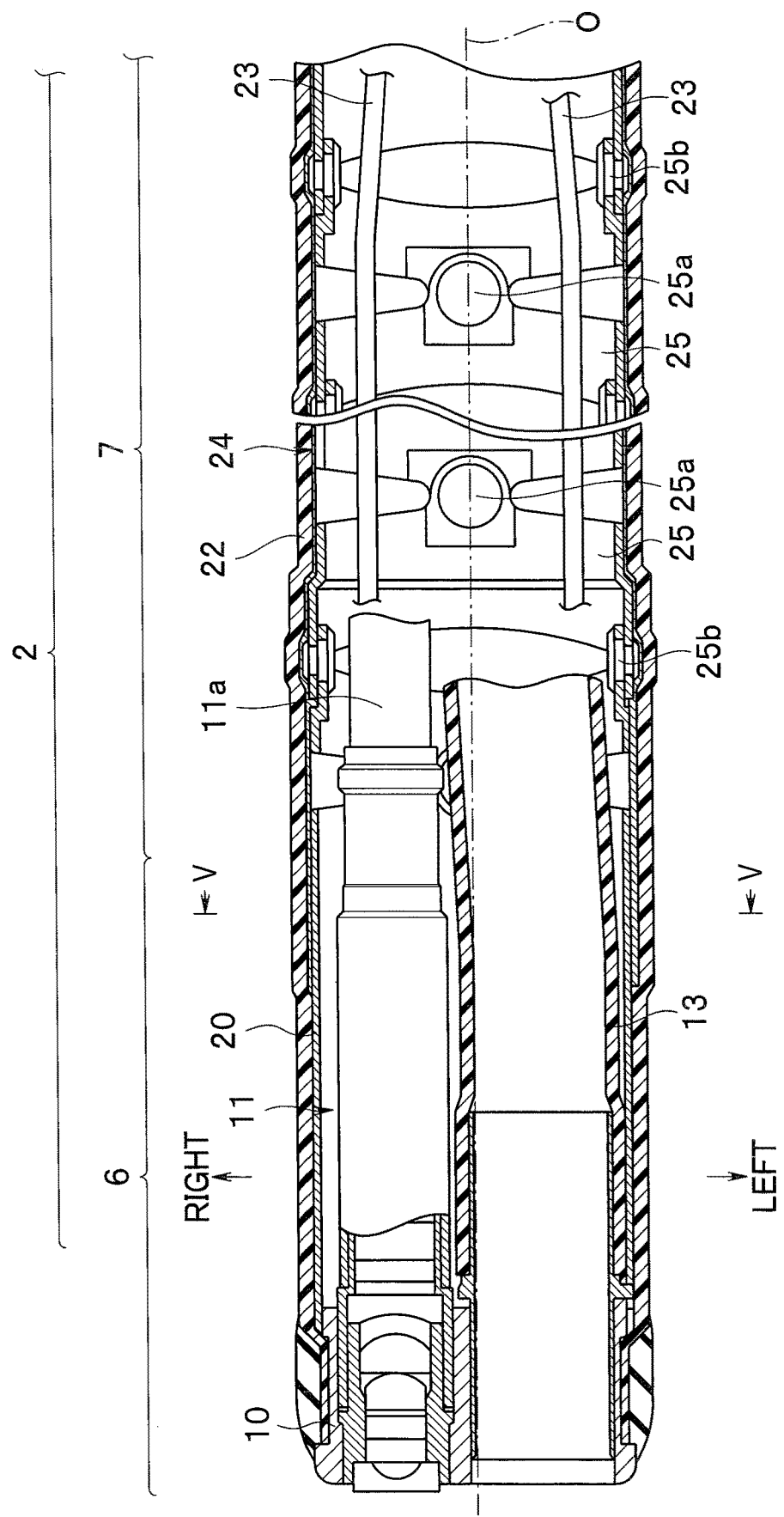
FIG. 4 is a transverse cross-sectional view showing main parts of a distal end portion and a bending portion.
Figure 5:
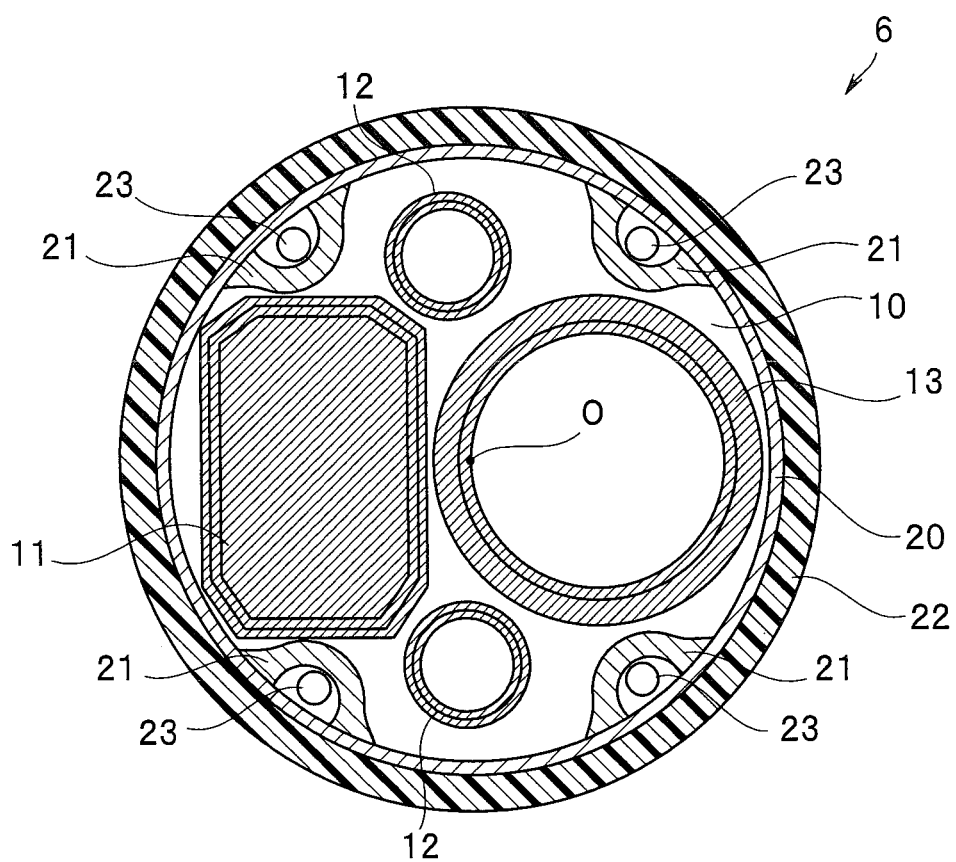
FIG. 5 is a cross-sectional view showing the distal end portion along line V-V in FIG. 4.
Figure 6:
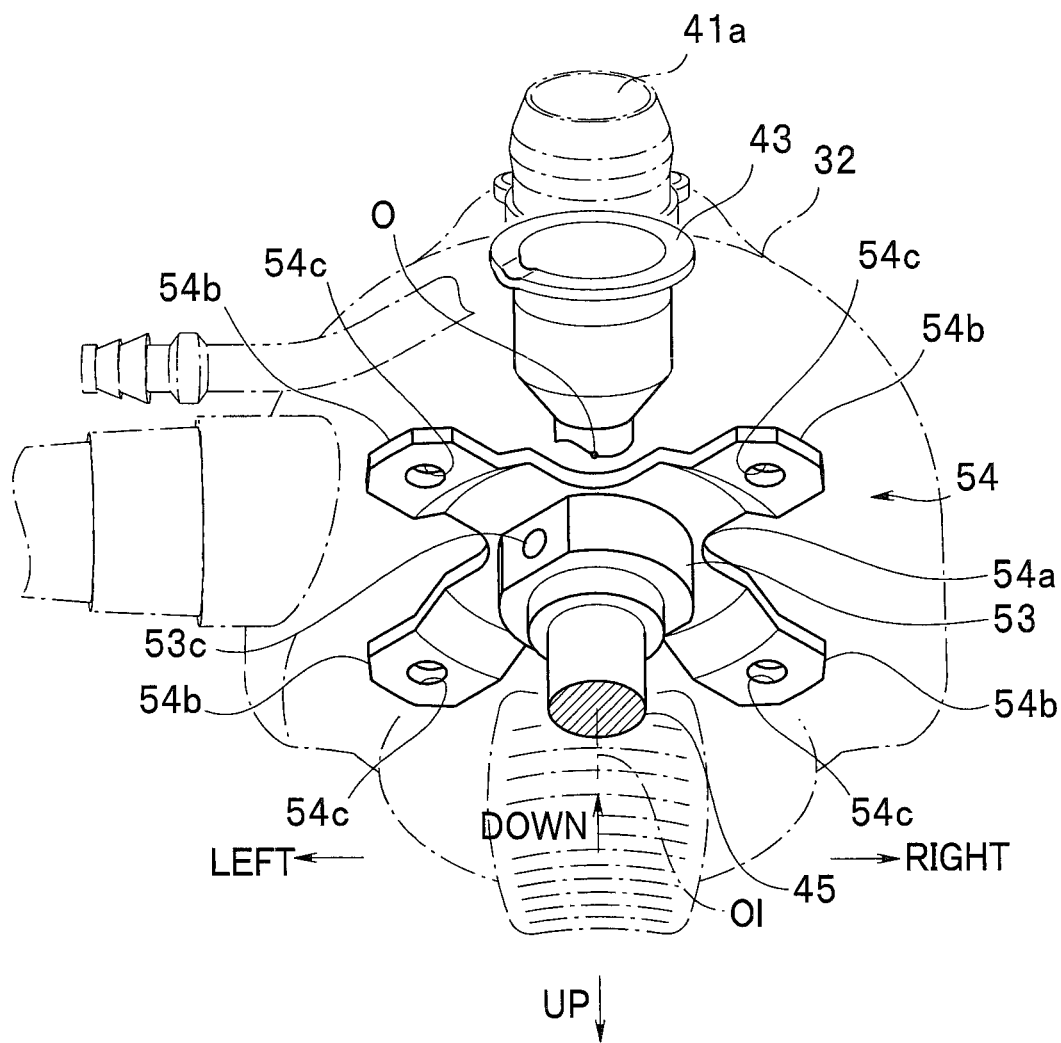
FIG. 6 is an explanatory view showing a positional relationship between a wire pulling member and a cylinder.
Figure 7:
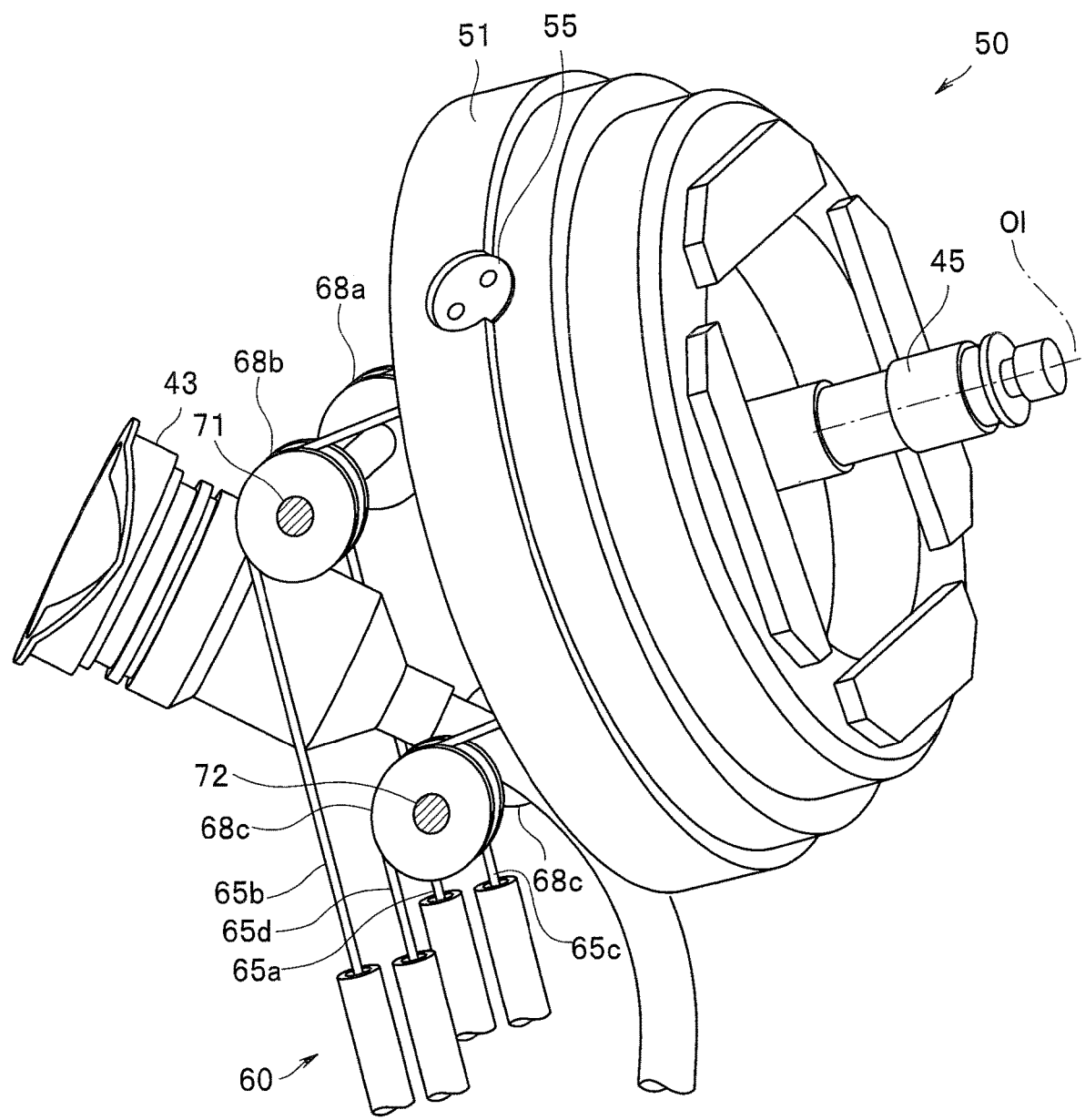
FIG. 7 is a perspective view showing a positional relationship between a wire pulling mechanism and the cylinder.
Figure 8:
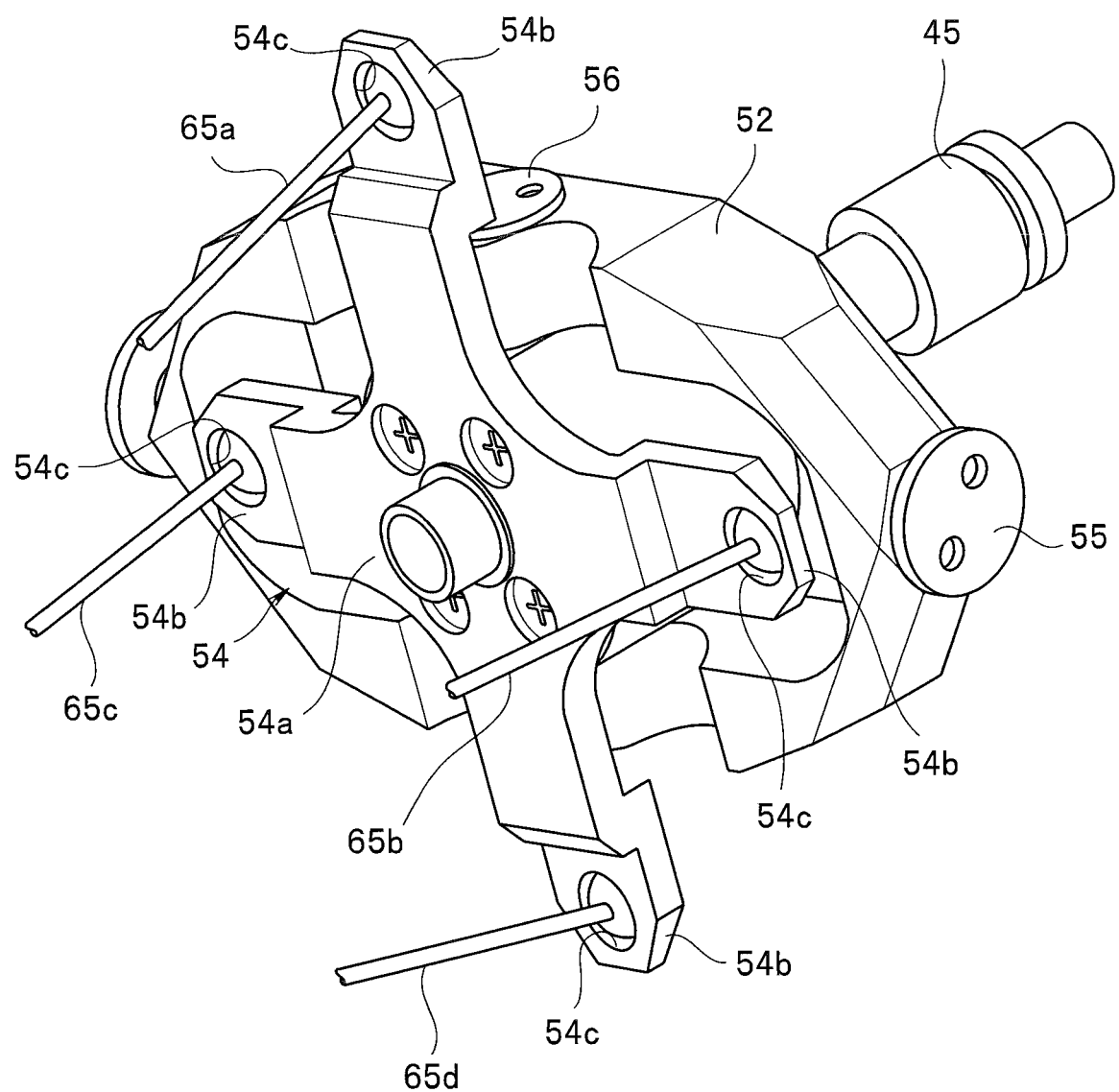
FIG. 8 is a perspective view showing internal structural components of the wire pulling mechanism.
Figure 9:
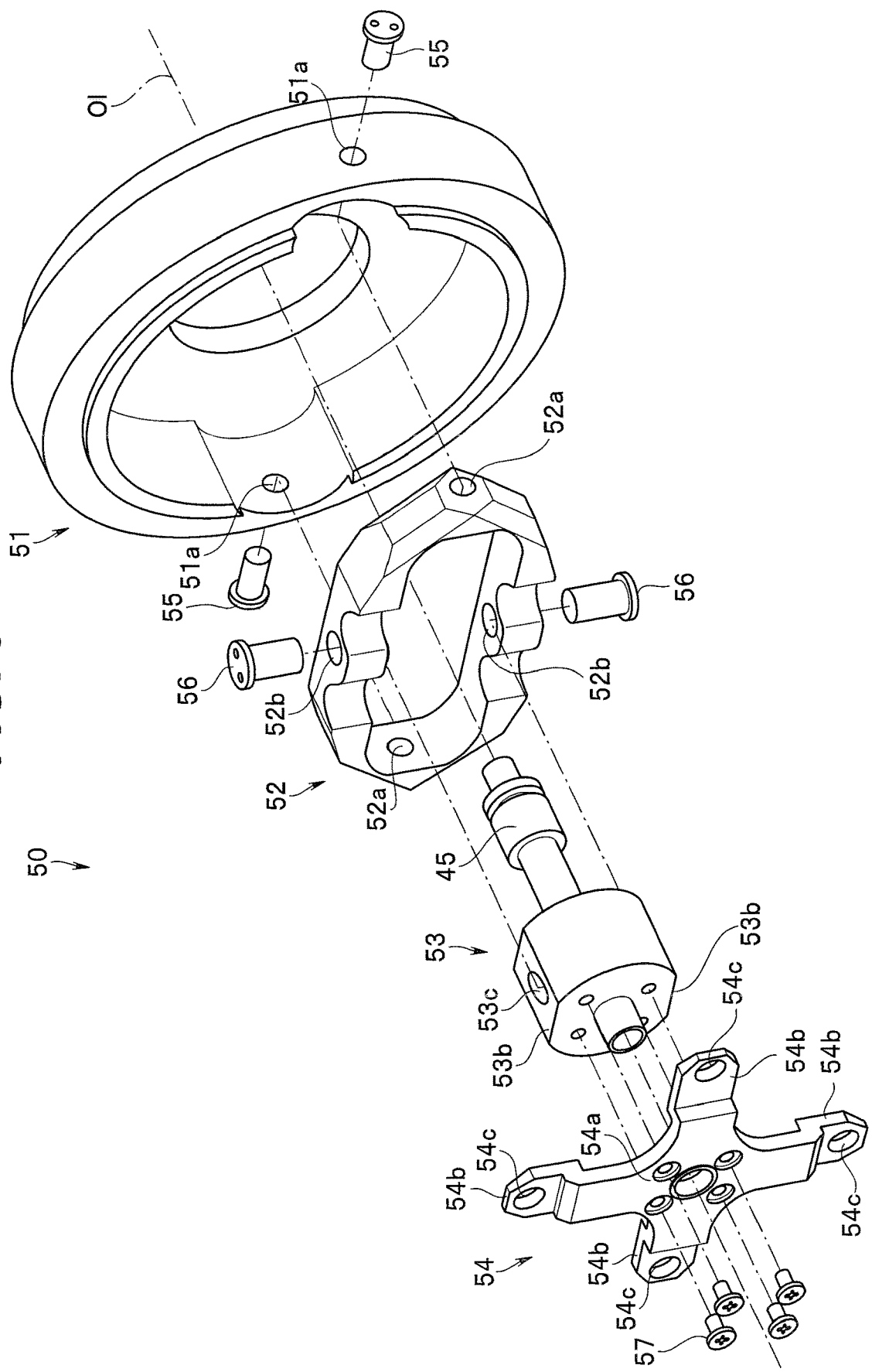
FIG. 9 is an exploded perspective view showing the internal structural components of the wire pulling mechanism.
Figure 10:
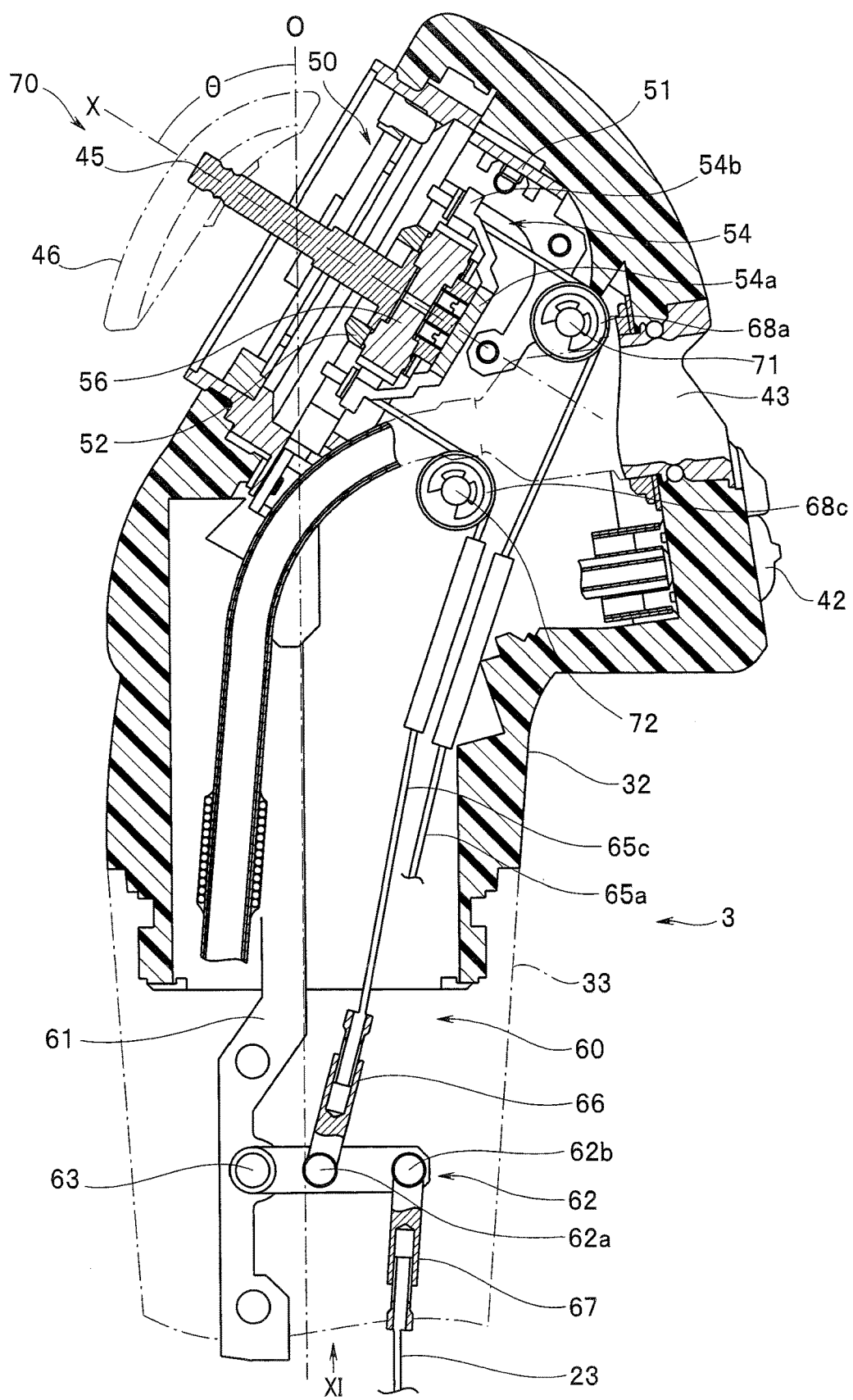
FIG. 10 is a cross-sectional view of main parts of an operation section.
Figure 11:
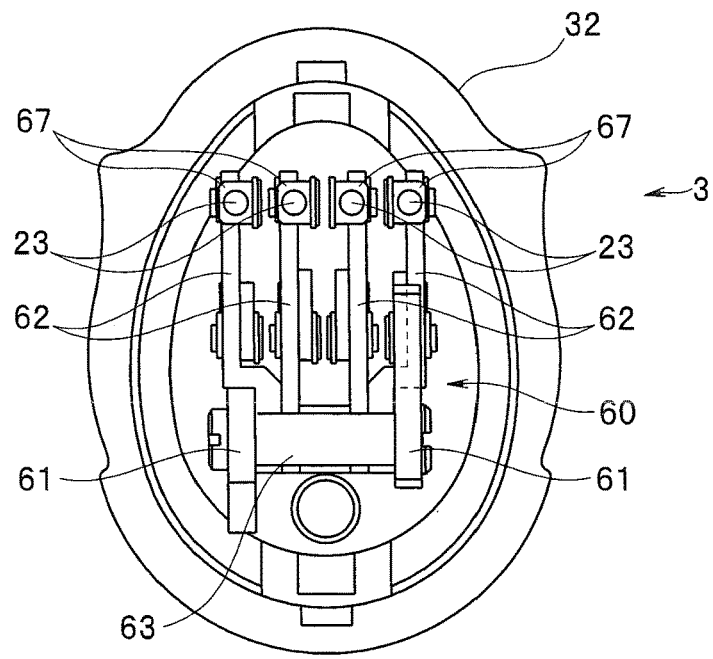
FIG. 11 is a view in the direction of arrow XI in FIG. 10.
Figure 12:
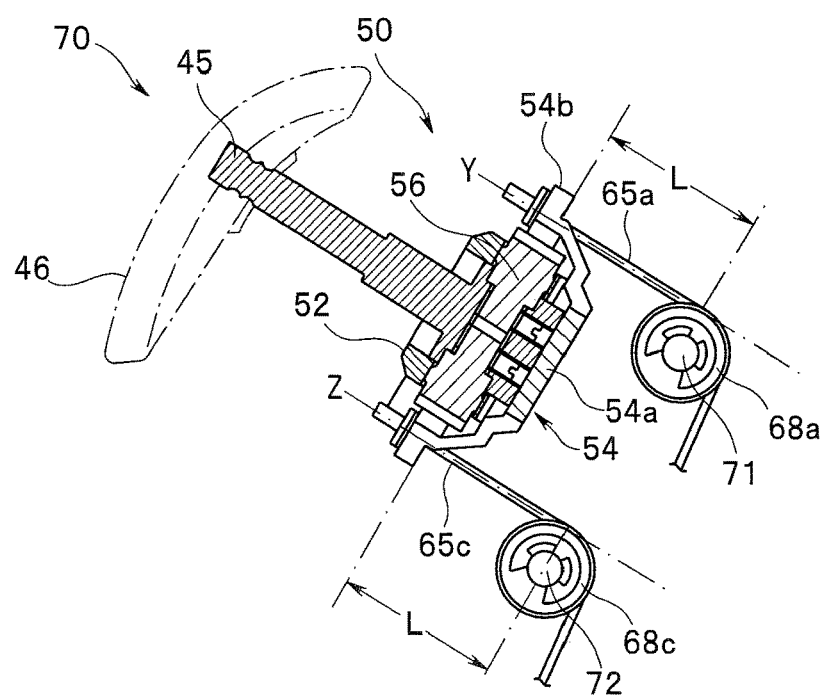
FIG. 12 is an explanatory view showing a bending operation device.
Figure 13:
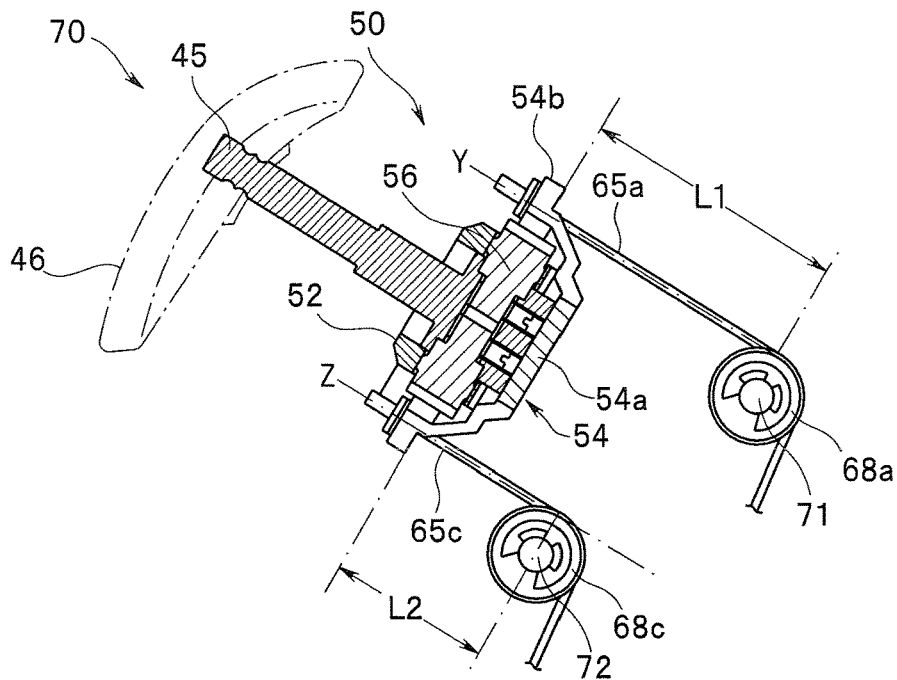
FIG. 13 is an explanatory view showing a bending operation device of a first modification.
Figure 14:
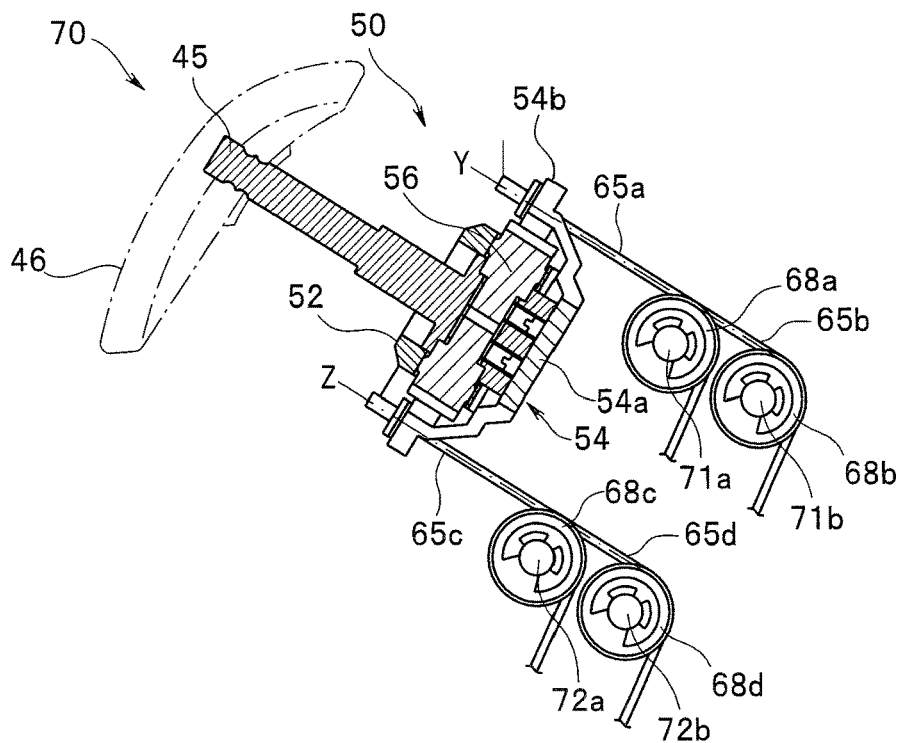
FIG. 14 is an explanatory view showing a bending operation device of a second modification.

Hereinafter, a mode of the present invention will be described with reference to the drawings. The drawings relate to an aspect of the present invention, and FIG. 1 is a front view showing an external appearance of an endoscope, FIG. 2 is a right side view showing the external appearance of the endoscope, FIG. 3 is a top view showing the external appearance of the endoscope, FIG. 4 is a transverse cross-sectional view showing main parts of a distal end portion and a bending portion, FIG. 5 is a cross-sectional view showing the distal end portion along line V-V in FIG. 4, FIG. 6 is an explanatory view showing a positional relationship between a wire pulling member and a cylinder, FIG. 7 is a perspective view showing a positional relationship between a wire pulling mechanism and the cylinder, FIG. 8 is a perspective view showing internal structural components of the wire pulling mechanism, FIG. 9 is an exploded perspective view showing the internal structural components of the wire pulling mechanism, FIG. 10 is a cross-sectional view of main parts of an operation section, FIG. 11 is a view in the direction of arrow XI in FIG. 10, FIG. 12 is an explanatory view showing a bending operation device, FIG. 13 is an explanatory view showing a bending operation device of a first modification, and FIG. 14 is an explanatory view showing a bending operation device of a second modification.

Figure 1:
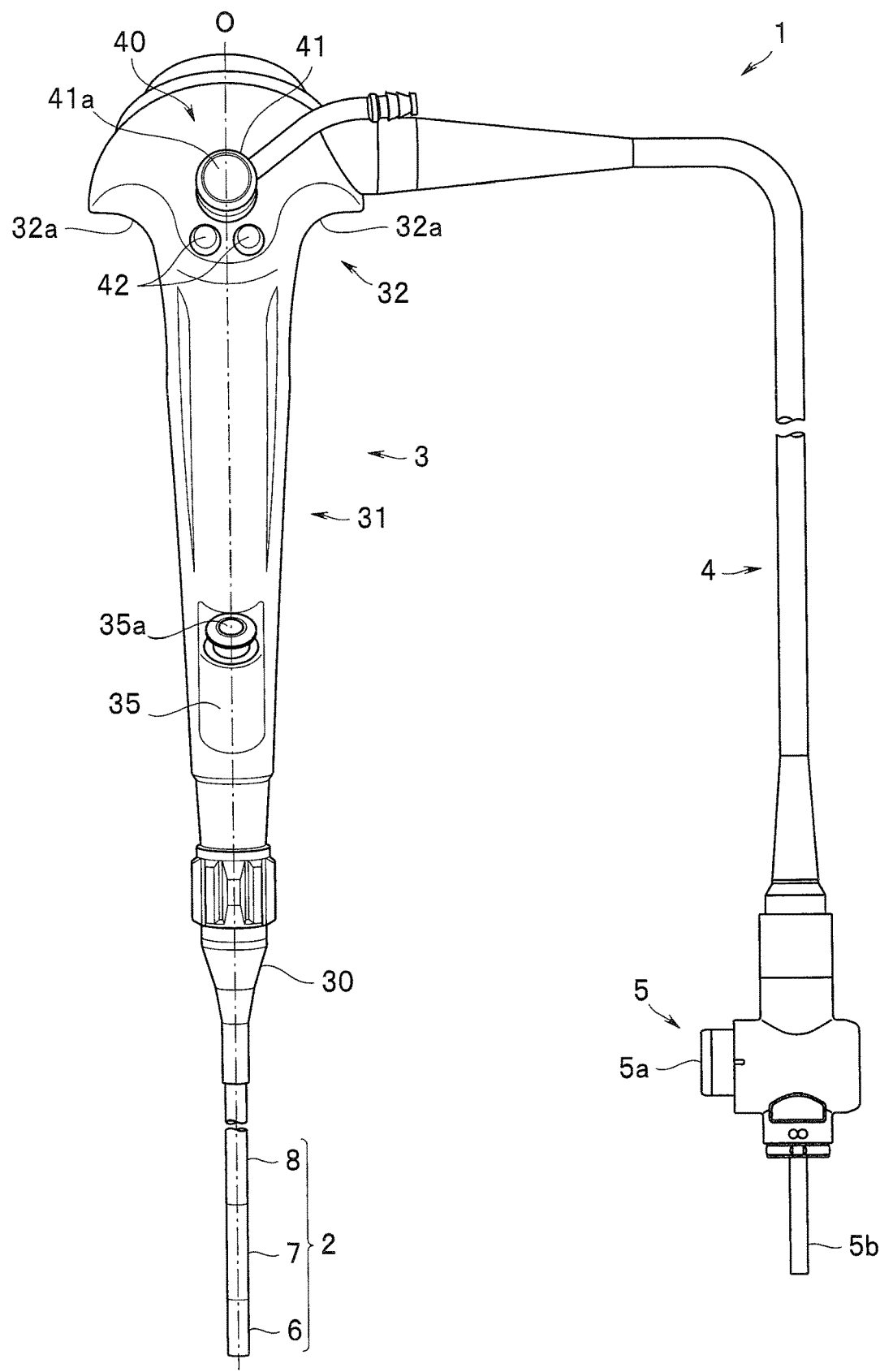
FIG. 1 is a front view showing an external appearance of an endoscope.
Figure 2:
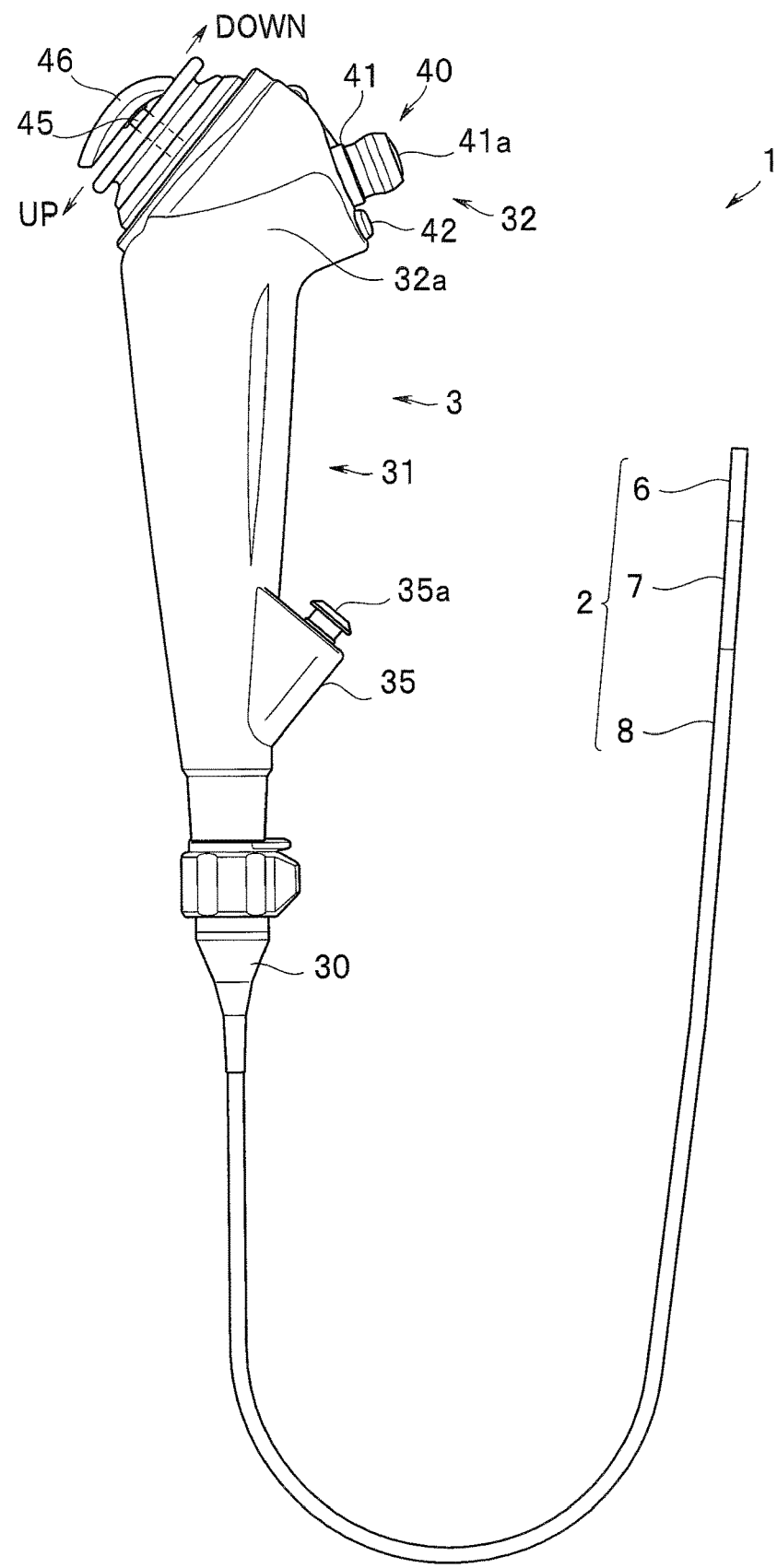
FIG. 2 is a right side view showing the external appearance of the endoscope.

As shown in FIGS. 1 and 2, an endoscope 1 of the present embodiment is an endoscope 1 for bronchus, and the endoscope 1 is configured by including an elongated tubular insertion section 2, an operation section 3 which is provided continuously to a proximal end of the insertion section 2, a universal cord 4 which is an endoscope cable extending from the operation section 3, and an endoscope connector 5 disposed at a distal end of the universal cord 4.

The insertion section 2 is configured by a flexible tubular member having a distal end portion 6, a bending portion 7, and a flexible tube portion 8 provided in a continuous manner from the distal end side.

The operation section 3 is configured by including a bend preventing portion 30 which is connected to the flexible tube portion 8 while covering a proximal end of the flexible tube portion 8, a grasping portion 31 which is provided continuously to the bend preventing portion 30 and which can be grasped by the hand of a user or the like, and an operation section main body 32 which is continuously provided on the proximal end side of the grasping portion 31.

Note that, in the present embodiment, directions and the like from an insertion axis O of the operation section 3 are defined relative to the state where the grasping portion 31 is grasped by a user or the like, and more specifically, front/back/right/left directions (a front surface, a back surface, right and left side surfaces, etc.) relative to the user or the like grasping the grasping portion 31 are defined for the operation section 3.

As shown in FIG. 1, the grasping portion 31 is formed into a shape that is right-left symmetrical with respect to the insertion axis O (center axis), and can be grasped in the same manner by either of the right and left hands of the user or the like.

Furthermore, a treatment instrument insertion portion 35 is provided on a front surface on the distal end side of the grasping portion 31. The treatment instrument insertion portion 35 is configured by including a treatment instrument insertion opening 35a through which various treatment instruments (not shown) are inserted.

The operation section main body 32 of the operation section 3 is formed expanded on the right and the left in a symmetrical manner about the insertion axis O, and a guide recess portion 32a which guides an index finger or the like of a user grasping the grasping portion 31 to an operation button group 40 is provided on each of the right and left side surfaces on the distal end side of the operation section main body 32.

Inside the operation section 3, the treatment instrument insertion opening 35a communicates with a treatment instrument insertion channel 13 (see FIG. 4), described below, via a branching member, not shown. Also, a forceps plug (not shown) which is a lid member configured to block the treatment instrument insertion opening 35a is freely attachable/detachable to/from the treatment instrument insertion portion 35.

The operation section main body 32 is configured, at the proximal end side of the grasping portion 31, by a hollow member having a substantially partially round shape which is expanded mainly on the right and left sides and the front side. The operation button group 40 used for realizing various functions of the endoscope 1 is provided on the front surface side of the operation section main body 32.

For example, the operation button group 40 is configured by including a suction button 41a protruding from a suction valve 41 which is detachably mounted on the operation section main body 32, and two button switches 42 to which arbitrary functions may be assigned from among various functions regarding the endoscope 1.

The suction button 41a and the button switches 42 are arranged in a right-left symmetrical manner on the front surface side of the operation section main body 32.

That is, the suction button 41a of the present embodiment is arranged at the center in the right-left width direction of the operation section main body 32 in a manner overlapping the insertion axis O.

Also, the two button switches 42 are arranged at right-left symmetrical positions across the insertion axis O, on the distal end side than the suction button 41a.

As shown in FIGS. 2 and 3, a bending lever 45 as an operation lever used for performing bending operation of the bending portion 7 is disposed on the rear surface side of the operation section main body 32.

For example, as shown in FIG. 3, with respect to the tilt direction of the bending lever 45, the right-left direction of tilt operation is defined to be the right-left width direction of the operation section 3, which is a direction orthogonal to the insertion axis O, and the up-down direction is defined to be the direction which is orthogonal to the right-left width direction.

More specifically, the tilt directions of the bending lever 45 of the present embodiment are defined, for example, with the left side as viewed in FIG. 3 as the tilt direction for bending the bending portion 7 to the left (left tilt direction), the right side as viewed in FIG. 3 as the tilt direction for bending the bending portion 7 to the right (right tilt direction), the bottom side as viewed in FIG. 3 as the tilt direction for bending the bending portion 7 upward (upward tilt direction), and the top side as viewed in FIG. 3 as the tilt direction for bending the bending portion 7 downward (downward tilt direction).

At a tip portion of the bending lever 45, a finger rest portion 46 where a thumb or the like of a user or the like is allowed to come into contact is provided.

The universal cord 4 extends from one side portion (for example, the left side portion) of the operation section main body 32. The universal cord 4 is a composite cable allowing insertion of various signal lines and the like which extend from the distal end portion 6 side to the operation section 3 through the inside of the insertion section 2 and which further extend from the operation section 3, allowing insertion of light guides 12 of a light source device (not shown), and allowing insertion of an air/water feeding tube extending from an air/water feeding device (not shown).

The endoscope connector 5 (see FIG. 1) provided at an end portion of the universal cord 4 is configured by including, at a side surface portion, an electrical connector portion 5a to which a signal cable that connects to a video processor (not shown) of an external appliance is connected, and by including a light source connector portion 5b to which a light guide and an electrical cable that connect to a light source device, which is an external appliance, are connected.

For example, as shown in FIGS. 4 and 5, a metal distal end rigid portion 10 is provided inside the distal end portion 6, and an image pickup unit 11 where an image pickup device, such as a CCD or a CMOS, is built in, a pair of light guides 12, and the treatment instrument insertion channel 13 are held in the distal end rigid portion 10.

Furthermore, inside the distal end portion 6, a most distal end bending piece 20 having the shape of a substantially circular cylinder is fitted on the proximal end side of the distal end rigid portion 10, and the outer circumference of the most distal end bending piece 20 is covered with bending rubber 22. Wire fixing portions 21 are provided on the inner circumference of the most distal end bending piece 20, at four positions around the insertion axis O, and distal ends of four bending operation wires 23 which serve as pulling wires and which are inserted in the insertion section 2 are fixed to the respective wire fixing portions 21.

To efficiently arrange each of the structural members without increasing the diameter of the distal end portion 6, the image pickup unit 11 and the treatment instrument insertion channel 13, which are large members, are arranged horizontally next to each other inside the distal end rigid portion 10 and the most distal end bending piece 20, and the light guides 12 are arranged, respectively, in spaces at the top and the bottom formed by the arrangement mentioned above.

Furthermore, to prevent interference of the image pickup unit 11 and the treatment instrument insertion channel 13 with each bending operation wire 23, each of the wire fixing portions 21 is provided at a position rotated by a predetermined angle, around the insertion axis O, from an up, down, left or right position of the distal end portion 6.

That is, as shown in FIG. 5, the respective wire fixing portions 21 are provided in the most distal end bending piece 20, at positions rotated to the left and the right respectively in the range of 30 degrees to 60 degrees from the up direction of the distal end portion 6, around the insertion axis O, and at positions rotated to the left and the right respectively in the range of 30 degrees to 60 degrees from the down direction of the distal end portion 6, around the insertion axis O, for example.

The bending portion 7 is configured to be able to actively bend in any direction from the insertion axis O, including the up-down/right-left directions, according to an operation input from a surgeon or the like to the operation section 3.

That is, the bending portion 7 of the present embodiment is configured by including a bending piece set 24 where a plurality of bending pieces 25 are coupled alternately by pivot portions 25a which are arranged in the up-down direction of the insertion section 2 and pivot portions 25b which are arranged in the right-left direction of the insertion section 2.

Inside the bending piece set 24, the signal cable 11a extending from the image pickup unit 11, the light guides 12, and the treatment instrument insertion channel 13 are inserted according to an arrangement substantially the same as the arrangement inside the distal end portion 6.

Furthermore, wire guides (not shown) allowing insertion of the respective bending operation wires 23 are formed to predetermined bending pieces 25 configuring the bending piece set 24, at substantially the same positions, around the insertion axis O, as the positions of the wire fixing portions 21 described above. Moreover, the outer circumference of the bending piece set 24 is covered with the bending rubber 22 extending from the distal end portion 6 side.

The flexible tube portion 8 is configured by a flexible tubular member which is capable of passively bending. The signal cable 11a, the light guides 12, and the treatment instrument insertion channel 13 (which are not shown in the drawing) are inserted in the flexible tube portion 8.

Next, the configuration of each portion built in the operation section 3 will be described in detail.

As shown in FIG. 6, a cylinder 43 which is provided continuously to the suction valve 41 is provided inside the operation section main body 32. The suction valve 41 can be detachably mounted on the cylinder 43, and the cylinder 43 is arranged at the center in the right-left width direction of the operation section main body 32 in a manner overlapping the insertion axis O in accordance with the arrangement of the suction button 41a.

For example, the bending lever 45 is configured by a joystick-type lever which can be tilted in any of the directions including up-down/right-left directions. The bending lever 45 is arranged on the rear surface side of the operation section main body 32, at a position where the bending lever 45 becomes right-left symmetrical.

That is, in the present embodiment, the bending lever 45 is arranged at the center in the right-left width direction of the operation section main body 32 in a manner overlapping the insertion axis O, and furthermore, as shown in FIG. 10, a lever axis X is at a predetermined angle θ with respect to a longitudinal direction (direction of the insertion axis O) of the operation section main body 32.

Also, as shown in FIGS. 7 to 10, inside the operation section 3, a wire pulling mechanism 50 is provided continuously to the proximal end side of the bending lever 45, and moreover, each bending operation wire 23 is connected to the wire pulling mechanism 50 via a relay lever mechanism 60.

The bending lever 45 constitutes, together with the wire pulling mechanism 50 and the relay lever mechanism 60, a bending operation device 70 (see FIGS. 7 and 8) configured to bend the bending portion 7 in an arbitrary direction.

As shown in FIGS. 7 to 10, the wire pulling mechanism 50 is configured by including a housing 51, a rotating frame 52 which is rotatably (swingably) and pivotally supported inside the housing 51, a base member 53 which is rotatably (swingably) and pivotally supported inside the rotating frame 52, and a wire pulling member 54 which is fixedly provided on the base member 53.

The housing 51 is formed by a member having a substantially circular cylindrical shape, and shaft holes 51*a* that face each other are provided piercing a circumferential wall of the housing 51.

The rotating frame 52 is formed by a frame body having a substantially rectangular shape, for example. A pair of screw holes 52*a* that face each other pierce the rotating frame 52 at the center of both end portions in the long side direction, and a pair of shaft holes 52*b* that face each other pierce the rotating frame 52 at the center of both end portions in the short side direction.

The rotating frame 52 is rotatably and pivotally supported by the housing 51 by screws 55 inserted in the respective shaft holes 51*a* of the housing 51 being screwed into the respective screw holes 52*a*.

The base member 53 is formed by a member having a substantially columnar shape. The bending lever 45 is integrally formed with the base member 53, at the center axis. Also, a pair of flat portions 53*b* that face each other are formed to a circumferential portion of the base member 53, and screw holes 53*c* are formed in a manner penetrating the flat portions 53*b*.

Screws 56 inserted through the respective shaft holes 52*b* of the rotating frame 52 are screwed into the screw holes 53*c*, and the base member 53 is thereby rotatably and pivotally supported by the rotating frame 52.

Moreover, the base member 53 is supported by the housing 51 via the rotating frame 52, and the bending lever 45 which is provided integrally and continuously to the base member 53 is thereby enabled to tilt in an arbitrary direction.

The wire pulling member 54 is formed by a plate member having arm portions 54*b* extending in four different directions. More specifically, in the present embodiment, the wire pulling member 54 is formed by a cross-shaped plate member where the angle formed by adjacent arm portions 54*b* is 90 degrees, and a center portion 54*a* is fixed to the base member 53 by screws 57.

That is, the bending lever 45 is coupled to the wire pulling member 54 via the base member 53, and the distal end side of each arm portion 54*b* is enabled to be displaced according to tilting motion of the bending lever 45.

Furthermore, a wire fixing hole 54*c* pierces the distal end side of each arm portion 54*b*, which is supported in a displaceable manner as described above. Note that the angle formed by the respective arm portions 54*b* is not limited to 90 degrees, and may be arbitrarily changed in the range of ±30 degrees from 90 degrees, for example.

The wire pulling mechanism 50 configured in the above manner is arranged inside the operation section main body 32 where the wire pulling mechanism 50 and the cylinder 43 face each other with one behind the other. In the present case, the wire pulling mechanism 50 is arranged with each arm portion 54*b* at a position rotated around a center axis O1 of the bending lever 45 in a range of 30 degrees to 60 degrees (for example, at a position rotated by 45 degrees) relative to the upward/downward/left/right tilt direction defined for the bending lever 45.

Accordingly, as shown in FIG. 7, the wire pulling mechanism 50 is arranged with the cylinder 43 facing between two arm portions 54*b* of the wire pulling member 54, for example.

As shown in FIGS. 10 and 11, the relay lever mechanism 60 is configured by including a pair of right and left stays 61 extending from the inside of the operation section main body 32 to the inside of a grasping portion 33, and four relay levers 62 which are supported by the stays 61.

The relay levers 62 are arranged in one line in the right-left direction inside the grasping portion 33, and the fixed end sides of the relay levers 62 are supported by a single shaft portion 63 which is installed between the right and left stays 61 as a fulcrum in a manner capable of swinging.

Each relay lever 62 corresponds to each arm portion 54*b* of the wire pulling mechanism 50, and a point of effort 62*a* to which the amount of displacement of each arm portion 54*b* according to the tilting motion of the bending lever 45 is transmitted through one of four bending operation wires 65*a*, 65*b*, 65*c*, 65*d* serving as a relay wire is set at a mid-point of each relay lever 62.

Moreover, a point of load 62*b* for amplifying the amount of displacement of each arm portion 54*b* and transmitting the amount of displacement to each bending operation wire 23 is set at the free end side of each relay lever 62, at a position separated from the fulcrum (shaft portion 63) than the point of effort 62*a*.

The respective bending wires 23 are aligned on the distal end sides of the relay levers 62 by a guide member (such as a coil pipe), not shown, so as to be coupled to the points of load 62*b* of the relay levers 62 while being substantially parallel to the insertion axis O.

More specifically, the proximal end side of the operation wire 65*a*, 65*b*, 65*c*, 65*d* is connected to the wire fixing hole 54*c* of each arm portion 54*b*. On the other hand, a screw-type first wire adjustment portion 66 configured to adjust the length of the operation wire 65*a*, 65*b*, 65*c*, 65*d* is provided at the point of effort 62*a* of each relay lever 62, and the distal end side of the operation wire 65*a*, 65*b*, 65*c*, 65*d* is connected to the point of effort 62*a* via the first wire adjustment portion 66.

Note that four pulleys 68*a*, 68*b*, 68*c*, 68*d* which are each pivotally supported by a rotation shaft 71, 72 inside the operation section main body 32 are engaged at mid-points of the respective operation wires 65*a*, 65*b*, 65*c*, 65*d* (see FIGS. 7 and 8).

Furthermore, a screw-type second wire adjustment portion 67 configured to adjust the length of each bending operation wire 23 is provided at the point of load 62*b* of each relay lever 62, and the proximal end side of each bending operation wire 23 is connected to the point of load 62*b* via the second wire adjustment portion 67. Note that the bending operation wires 23 are routed inside the insertion section 2 with the distal end sides crossed between up and down and right and left.

According to such a configuration, for example, when a user or the like grasps the grasping portion 31 of the operation section 3 and tilts the bending lever 45 in the left tilt direction by the thumb of the grasping hand, the two operation wires 65*a*, 65*c* coupled to the two arm portions 54*b* positioned in the right tilt direction are mainly pulled/slackened.

The pull on the two operation wires 65*a*, 65*c* is transmitted to the corresponding relay levers 62, and the respective relay levers 62 are caused to swing at an angle according to the amount of pulling/slackening. Accordingly, inside the bending portion 7, the two bending operation wires 23 positioned on the left side in the bending direction are mainly pulled/slackened by the amount of pulling/slackening amplified by the relay levers 62, and the bending portion 7 is bent to the left.

Moreover, for example, when a user or the like grasps the grasping portion 31 of the operation section 3 and tilts the bending lever 45 in the right tilt direction by the thumb of the grasping hand, the two operation wires 65b, 65d coupled to the two arm portions 54b positioned in the left tilt direction are mainly pulled/slackened.

The pull on the two operation wires 65b, 65d is transmitted to the corresponding relay levers 62, and the respective relay levers 62 are caused to swing at an angle according to the amount of pulling/slackening. Accordingly, inside the bending portion 7, the two bending operation wires 23 positioned on the right side in the bending direction are mainly pulled/slackened by the amount of pulling/slackening amplified by the relay levers 62, and the bending portion 7 is bent to the right.

Moreover, for example, when a user or the like grasps the grasping portion 31 of the operation section 3 and tilts the bending lever 45 in the upward tilt direction by the thumb of the grasping hand, the operation wires 65c, 65d coupled to the two arm portions 54b positioned in the downward tilt direction are mainly pulled/slackened.

The pull on the two operation wires 65c, 65d is transmitted to the corresponding relay levers 62, and the respective relay levers 62 are caused to swing at an angle according to the amount of pulling/slackening. Accordingly, inside the bending portion 7, the two bending operation wires 23 positioned on the bottom side in the bending direction are mainly pulled/slackened by the amount of pulling/slackening amplified by the relay levers 62, and the bending portion 7 is bent downward.

Moreover, for example, when a user or the like grasps the grasping portion 31 of the operation section 3 and tilts the bending lever 45 in the downward tilt direction by the thumb of the grasping hand, the operation wires 65a, 65b coupled to the two arm portions 54b positioned in the upward tilt direction are mainly pulled/slackened.

The pull on the two operation wires 65a, 65b is transmitted to the corresponding relay levers 62, and the respective relay levers 62 are caused to swing at an angle according to the amount of pulling/slackening. Accordingly, inside the bending portion 7, the two bending operation wires 23 positioned on the top side in the bending direction are mainly pulled/slackened by the amount of pulling/slackening amplified by the relay levers 62, and the bending portion 7 is bent upward.

According to such an embodiment, the bending operation device 70 is configured including the bending lever 45 which is supported in a manner capable of tilting with respect to the operation section 3 of the endoscope 1, the arm portions 54b which are provided on the bending lever 45 and distal end sides of which are capable of being displaced according to tilting motion of the bending lever 45, and the relay levers 62 which are supported in a manner capable of swinging with respect to the operation section 3, which include, at mid-points, the points of effort 62a to which the distal end sides of the arm portions 54b are connected via the respective operation wires 65a, 65b, 65c, 65d, and which include the points of load 62b, to which the bending operation wires 23 are connected, at positions separated from the fulcrum (shaft portion 63) than the points of effort 62a, and thus, the bending portion 7 may be caused to bend at a sufficient bending angle without increasing the size and the length of the arm portions 54b.

That is, by transmitting the amount of displacement (the amount of pulling/slackening) by the arm portions 54b to the bending operation wires 23 after amplifying the amount by the relay levers 62, the bending portion 7 may be caused to bend by a sufficient amount of pulling/slackening without increasing the size and the length of the arm portions 54b. Accordingly, interference between the arm portions 54b and other internal components may be prevented, and moreover, an increase in the size of the operation section 3 may be effectively suppressed.

Furthermore, by causing the stays 61 to extend from the operation section main body 32 side to the grasping portion 33 side, and providing the relay levers 62 configured to amplify the amount of pulling/slackening of the arm portions 54b in the grasping portion 33, the dead space inside the operation section 3 may be effectively utilized. In addition, by arranging, and pivotally supporting, the respective relay levers 62 on the single shaft portion 63, the relay levers 62 may be collected and arranged at one position.

Furthermore, by providing, to the relay lever mechanism 60, the first wire adjustment portion 66 configured to adjust the length of the respective operation wires 65a, 65b, 65c, 65d connected to the point of effort 62a of the respective relays lever 62 and the second wire adjustment portion 67 configured to adjust the length of the respective bending operation wires 23 connected to the point of load 62b of the respective relay levers 62, the relationship between the tilted state of the bending lever 45 and the bent state of the bending portion 7 may be easily tuned.

That is, at the relay lever mechanism 60 of the present embodiment including the first and the second wire adjustment portions 66, 67, the relationship between the tilted state of the bending lever 45 and the bent state of the bending portion 7 is roughly adjusted by adjustment of the lengths of the operation wires 65a, 65b, 65c, 65d by the first wire adjustment portions 66, and then, the relationship may be finely adjusted by the adjustment of the lengths of the bending operation wires 23 by the second wire adjustment portions 67, and a tuning operation is facilitated.

Particularly, in the present case, the relay levers 62 are collected and arranged inside the grasping portion 33, and the first and the second wire adjustment portions 66, 67 are arranged being coupled to the points of effort 62a and the points of load 62b of the respective relay levers 62, and thus, all the wire adjustment portions 66, 67 may be easily accessed by a simple operation of removing the grasping portion 33 from the operation section main body 32 without having to disassemble the operation section main body 32.

Note that the bending operation device 70 does not have to be provided with the relay lever mechanism described above, and may be configured in such a manner that the four bending operation wires 23 serving as the pulling wires are directly connected to the respective arm portions 54b of the wire pulling member 54.

In the following, the arrangement of the four operation wires 65a, 65b, 65c, 65d, provided in the bending operation device 70 of the present embodiment, connected to the four arm portions 54b of the wire pulling member 54 and the four pulleys 68a, 68b, 68c, 68d, provided in the bending operation device 70, configured to change the extending directions of the four operation wires 65a, 65b, 65c, 65d inside the operation section 3 will be described in further detail.

As shown in FIGS. 6 and 7, the wire pulling mechanism 50 of the bending operation device 70 is arranged inside the operation section main body 32 where the wire pulling mechanism 50 and the cylinder 43, which is provided continuously to the suction valve 41, face each other with one behind the other, and the four arm portions 54b of the wire pulling member 54 are arranged, in the present case, at positions rotated by 45 degrees around the center axis O1 of the bending lever 45, the lever axis X of which is at the predetermined angle θ with respect to the longitudinal direction (direction of the insertion axis O) of the operation section main body 32. Moreover, in the present case, the cylinder 43 is arranged facing between two arm portions 54b on the upper side of the wire pulling member 54.

Accordingly, as shown in FIGS. 7 and 10, with the bending operation device 70, each of the pulleys 68a, 68b, 68c, 68d is pivotally supported by the rotation shaft 71, 72 in such a way that each of the operation wires 65a, 65b, 65c, 65d connected to the four arm portions 54b of the wire pulling member 54 does not interfere with the cylinder 43 inside the operation section main body 32.

Note that, with the bending operation device 70, the two pulleys 68a, 68b at positions on the proximal end side of the operation section 3 are pivotally and coaxially supported by one common rotation shaft 71, and the two pulleys 68c, 68d at positions on the distal end side of the operation section 3 are pivotally and coaxially supported by one common rotation shaft 72.

Alternatively, at least the two pulleys 68a, 68b for changing the directions of the frequently used two operation wires 65a, 65b for bending the bending portion 7 upward may be pivotally and coaxially supported by one common rotation shaft 71, or the pulleys 68a, 68b, 68c, 68d may each be pivotally supported by a different rotation shaft.

Note that both end portions of the rotation shaft 71 are held by a frame member, not shown. The inside of the operation section 3 is partitioned by the frame member into a space where the wire pulling member 54 and the operation wires 65a, 65b, 65c, 65d are disposed and a space where other internal components (the light guides 12, the treatment instrument insertion channel 13, and the like) are disposed, and the internal components are prevented from interfering with the wire pulling member 54, the operation wires 65a, 65b, 65c, 65d, and the like.

When the bending lever 45, the lever axis X of which is at the predetermined angle θ with respect to the longitudinal direction (direction of the insertion axis O) of the operation section main body 32, is in a neutral state where the bending portion 7 is substantially straight (see FIG. 10), the pulleys 68a, 68b, 68c, 68d are arranged, pivotally supported by the rotation shafts 71, 72 inside the operation section main body 32, at positions at which wire axes of the respective operation wires 65a, 65b, 65c, 65d (only wire axes Y, Z of the operation wires 65a, 65c are shown) are oriented toward the respective arm portions 54b while being substantially parallel to one another, as shown in FIG. 12.

In other words, in the neutral state of the bending lever 45, the lever axis X of which is at the predetermined angle θ with respect to the longitudinal direction (direction of the insertion axis O) of the operation section main body 32, where the bending portion 7 is substantially straight, the respective pulleys 68a, 68b, 68c, 68d are provided at positions at which the wire axes of the respective operation wires 65a, 65b, 65c, 65d (only the wire axes Y, Z of the operation wires 65a, 65c are shown in FIG. 12) are incident on the respective arm portions 54b at the same angle (for example, an angle within an error range of about ±20 degrees with respect to the perpendicular direction of the arm portions 54b) while being substantially parallel to one another.

Moreover, the positions of the respective pulleys 68a, 68b, 68c, 68d are set such that extension lengths L of the respective operation wires 65a, 65b, 65c, 65d to the corresponding arm portions 54b are made substantially the same. Note that, in FIG. 12, the two pulleys 68b, 68d and the two operation wires 65b, 65d are at a dead angle due to the two pulleys 68a, 68b and the two operation wires 65a, 65b.

In the present case, the disposed positions of the respective pulleys 68a, 68b, 68c, 68d are set such that the wire axes of the respective operation wires 65a, 65b, 65c, 65d (only the wire axes Y, Z of the operation wires 65a, 65c are shown in FIG. 12) are incident at a substantially orthogonal (≈90 degrees) angle at which the directions are substantially perpendicular to the extending directions of the arm portions 54b.

That is, with the bending operation device 70, the pulleys 68a, 68b, 68c, 68d, which engage with mid-points of the respective operation wires 65a, 65b, 65c, 65d, are provided inside the operation section main body 32, and in the neutral state of the bending lever 45, which is provided inclined at a predetermined angle with respect to the longitudinal direction (direction of the insertion axis O) of the operation section main body 32, where the bending portion 7 is made substantially straight by the pulleys 68a, 68b, 68c, 68d, the operation wires 65a, 65b, 65c, 65d are substantially parallel to one another, and are oriented substantially perpendicularly with respect to the extending direction of the arm portions 54b.

Accordingly, with the endoscope 1, because the four operation wires 65a, 65b, 65c, 65d extending to the respective arm portions 54b are set to be substantially parallel to one another and to have substantially the same lengths L by the respective pulleys 68a, 68b, 68c, 68d provided in the bending operation device 70, the amount of pulling/slackening by the amount of displacement of the respective arm portions 54b by the tilting operation of the bending lever 45 is made uniform for the four operation wires 65a, 65b, 65c, 65d, and the bending operation of the bending portion 7 may be stably performed.

Moreover, each operation wire 65a, 65b, 65c, 65d is incident, with respect to the extending direction of the respective arm portions 54b, at a substantially orthogonal (≈90 degrees) angle along a substantially perpendicular direction, and thus, the operation section main body 32 does not have to be made unnecessarily large, and the size of the operation section main body 32 for achieving an angle allowing the bending portion 7 to be bent in a desirable manner may be optimized and an increase in the size of the operation section 3 may be prevented.

As described above, the endoscope 1 may be configured such that, by providing the bending operation device 70 of the present embodiment to the operation section main body 32 of the operation section 3, an increase in the size of the operation section 3 is prevented, the amount of pulling/slackening by the amount of displacement by tilting of the bending lever 45 is made uniform for the plurality of operation wires 65a, 65b, 65c, 65d, and an amount of pulling/slackening of the operation wires 65a, 65b, 65c, 65d sufficient for bending the bending portion 7 to a desired bending angle can be achieved.

First Modification

Note that, as shown in FIG. 13, the position of each pulley 68a, 68b, 68c, 68d may be set such that substantially same extension lengths L1 of the two operation wires 65a, 65b to the corresponding arm portions 54b and substantially same extension lengths L2 of the two operation wires 65c, 65d to the corresponding arm portions 54b are different, with the lengths L1 being longer than the lengths L2 (L1>L2) in the present case.

Also in the present case, the two pulleys 68b, 68d and the two operation wires 65b, 65d are at a dead angle in FIG. 13, due to the two pulleys 68a, 68b and the two operation wires 65a, 65b.

Second Modification

Also, as shown in FIG. 14, the pulleys 68a, 68b, 68c, 68d may be pivotally supported by different rotation shafts 71a, 71b, 72a, 72b, respectively.

Note that, according to such a configuration, the position of each pulley 68a, 68b, 68c, 68d may be set such that the extension lengths of the respective operation wires 65a, 65b, 65c, 65d to the corresponding arm portions 54b are all different.

Note that the present invention is not limited to each embodiment described above, and various modifications and changes may be made within the technical scope of the present invention.

What is claimed is:

1. A bending operation device comprising:
   a bending lever that is tiltably supported with an angle to a longitudinal direction of an operation section of an endoscope;
   a wire pulling member that is provided inside the operation section, and includes a plurality of arms that are displaced according to a tilting motion of the bending lever;
   a plurality of operation wires that are connected to the plurality of arms, respectively, and bend, by being pulled/slackened according to displacement of the wire pulling member, a bending portion that is provided in an insertion section of the endoscope; and
   a plurality of pulleys that are provided inside the operation section, the plurality of pulleys being configured to change the directions of the plurality of operation wires, respectively,
   wherein the plurality of pulleys are disposed at positions such that each of the plurality of operation wires respectively connected to the plurality of arms are parallel to one another in a region between the plurality of pulleys and the plurality of arms when the bending lever is in a neutral position at which the bending portion is substantially straight,
   among the plurality of pulleys, a pair of first pulleys are pivotally supported by a same first rotation shaft, the pair of first pulleys being configured to change directions of a pair of first operation wires among the plurality of operation wires, the pair of first operation wires being for bending the bending portion upward, and
   among the plurality of pulleys, a pair of second pulleys are pivotally supported by a same second rotation shaft that is different from the first rotation shaft, the pair of second pulleys being different from the pair of first pulleys and configured to change directions of a pair of second operation wires among the plurality of operation wires, the pair of second operation wires being different from the pair of first operation wires and are for bending the bending portion downward.

2. The bending operation device according to claim 1, wherein the wire pulling member is arranged at a position rotated around a center axis of the bending lever so that the plurality of arms and a cylinder of a suction valve provided in the operation section do not interfere with each other.

3. The bending operation device according to claim 1, wherein the plurality of pulleys are disposed at positions at which the plurality of operation wires are connected while extending in a direction substantially orthogonal to the plurality of arms.

4. The bending operation device according to claim 1, wherein the plurality of pulleys are disposed at positions at which lengths of the plurality of operation wires to the plurality of arms are substantially same.

5. An endoscope comprising the bending operation device according to claim 1.

* * * * *